United States Patent [19]

Kolts

[11] 4,394,297
[45] Jul. 19, 1983

[54] ZINC TITANATE CATALYST
[75] Inventor: John H. Kolts, Bartlesville, Okla.
[73] Assignee: Phillips Petroleum Company, Bartlesville, Okla.
[21] Appl. No.: 430,628
[22] Filed: Sep. 30, 1982

Related U.S. Application Data

[62] Division of Ser. No. 267,230, May 26, 1981, Pat. No. 4,368,344.
[51] Int. Cl.³ .................. B01J 27/14; B01J 23/08; H01B 1/06
[52] U.S. Cl. ....................... 252/437; 252/435; 252/463; 252/520
[58] Field of Search ............... 252/435, 437, 463, 520

[56] References Cited

U.S. PATENT DOCUMENTS 3,842,018  10/1974  Ichinose et al. ............ 252/520
3,899,451  8/1975  Ichinose et al. ............ 252/520
4,086,556  4/1978  Nitto et al. ............... 252/520 X Primary Examiner—Delbert E. Gantz
Assistant Examiner—William G. Wright

[57] ABSTRACT

The catalytic oxidative dehydrogenation of at least one dehydrogenatable organic compound which has at least one

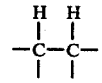

grouping is carried out in the presence of a zinc titanate catalyst. The selectivity of the zinc titanate catalyst may be improved by a promoter at least one member of which is selected from the group consisting of chromium, antimony, bismuth, aluminum, phosphorus, indium, tin, lanthanum and cerium.

6 Claims, No Drawings

ZINC TITANATE CATALYST

This application is a division of application Ser. No. 267,230, filed May 26, 1981, now U.S. Pat. No. 4,368,344.

This invention relates to an improved catalytic process for the oxidative dehydrogenation (OXD) of organic compounds, and a catalyst therefor.

OXD processes for the conversion of organic compounds to compounds having a higher degree of unsaturation are well known. A number of different catalyts have been proposed for OXD and research continues.

In accordance with the present invention, free oxygen is mixed with a dehydrogenatable organic compound and the resulting mixture is passed in contact with a zinc titanate catalyst to convert the organic compounds to compounds having a higher degree of unsaturation. The zinc titanate catalyst may be formed by combining zinc oxide and titanium dioxide by any of the methods known in the art for forming zinc titanate. A promoter may be added to the zinc titanate, if desired, to improve the selectivity of the zinc titanate.

The oxidative dehydrogenation process is carried out as a continuous process. The term "continuous process" is utilized to refer to a process in which the mixture of oxygen and the organic compounds is continuously passed over the zinc titanate catalyst for substantial periods of time without the need for periodic regeneration of the zinc titanate catalyst as would be required by a cyclic process.

Other objects and advantages of the invention will be apparent from the foregoing brief description of the invention and the appended claims as well as from the detailed description of the invention which follows:

The organic feedstocks which can be oxidatively dehydrogenated in accordance with the present invention are dehydrogenatable organic compounds having from 2 to 12 carbon atoms per molecule and characterized by having at least one

grouping, i.e., adjacent carbon atoms, each having at least one hydrogen atom. Suitable compounds include paraffins, olefins, cycloaliphatics and alkyl aromatic compounds having from 2 to 12 carbon atoms per molecule. Particularly suitable are paraffins having from 2 to 5 carbon atoms per molecule and monoolefins having from 4 to 5 carbon atoms per molecule, branched or unbranched. Some examples of suitable hydrocarbon feedstocks are ethane, propane, butane, isobutane, pentane, isopentane, hexane, 2-methylhexane, n-octane, n-dodecane, 1-butene, 2-bentene, 2-methyl-butene-1, 2-methyl-butene-2, 2-hexene, 1-octene, 3-methylnonene-4, 1-dodecene, cyclohexane, and the like and mixtures of any two or more thereof. Particularly appropriate is the conversion of ethane to ethylene, propane to propylene, butanes to butenes and butadiene, butenes to butadiene, and isopentane to isoamylenes and isoprene.

The free oxygen required for the OXD process may be obtained from any suitable source. Typically, air is mixed with the hydrocarbon feedstock to provide the required oxygen.

The dehydrogenation catalyst employed in the process of the present invention is a composition comprising zinc and titanium wherein the zinc and titanium are present in the catalyst composition in the form of zinc titanate. A promoter may be added to the catalyst composition to improve the selectivity of the zinc titanate. The promoter which may be used is as least one member selected from the group consisting of chromium, antimony, bismuth, aluminum, phosphorus, indium, tin, lanthanum, and cerium.

The zinc titanate may be prepared by intimately mixing suitable portions of zinc oxide and titanium dioxide, preferably in a liquid such as water, and calcining the mixture in the presence of free oxygen at a temperature in the range of about 650° C. to about 1050° C., preferably in the range of about 675° C. to about 975° C. A calcining temperature in the range of about 800° C. to about 850° C. is most preferred because the surface area of the catalyst is maximized in this temperature range thus producing a more active catalyst. The titanium dioxide used in preparing the zinc titanate preferably has extremely fine particle size to promote intimate mixing of the zinc oxide and titanium dioxide. This produces a rapid reaction of the zinc oxide and titanium dioxide which results in a more active catalyst. Preferably the titanium dioxide has an average particle size of less than 100 millimicrons and more preferably less than 30 millimicrons. Flame hydrolyzed titanium dioxide has extremely small particle size and is particularly preferred in preparing the catalyst. The atomic ratio of zinc to titanium will generally lie in the range of about 1:1 to about 3:1 and will preferably lie in the range of about 1.7:1 to about 2.1:1 because the activity of the catalyst is greatest for atomic ratios of zinc to titanium in this range. The term "zinc titanate" is used regardless of the atomic ratio of zinc to titanium.

The zinc titanate may also be prepared by coprecipitation from aqueous solutions of a zinc compound and a titanium compound. The aqueous solutions are mixed together and the hydroxides are precipitated by the addition of ammonium hydroxide. The precipitate is then washed, dried and calcined as described in the preceding paragraph. This method of preparation is less preferred than the mixing method because the zinc titanate prepared by the coprecipitation method is softer than the zinc titanate prepared by the mixing method.

If a promoter is used, the promoter is present on the catalyst in the oxide form. The promoter can be added to the zinc titanate as powdered oxide and dispersed by any method known in the art such as rolling, shaking or stirring. The preferred method of adding the promoter is by impregnating the preformed zinc titanate with a solution of a compound of the promoting element, or compounds containing the promoting elements to be mixed that becomes converted to the oxide during subsequent preparation of the catalyst.

The concentration of the promoter expressed as an element or mixtures of elements, can be any suitable concentration. The concentration of the promoter expressed as an element, will generally be in the range of about 0.3 to about 10 weight percent based on the weight of the zinc titanate prior to treatment with the promoter and will preferably be in the range of about 0.5 to about 5 weight percent based on the weight of the zinc titanate. The promoting elements are preferably used singularly and not in combinations. Except for antimony, which apparently does not form nitrate compounds, the nitrates can conveniently provide a suitable form of the promoter with which to impregnate the zinc titanate. The salts of organic acids such as acetates, butyrates, or benzoates also can conveniently provide a suitable form of the promoter with which to impregnate the zinc titanate. Other suitable compounds of antimony are antimony tartrate, potassium antimonyl tartrate, and the like and mixtures of any two or more thereof. Tin can be added as stannous or stannic chloride. Phosphorus can conveniently be added as phosphoric acid or as an ammonium salt such as monobasic or dibasic ammonium phosphate. Following impregnation with a solution of the promoting element or elements, solvent is removed by warming, and the dried product is then calcined in a free oxygen-containing environment at about 800° C. to convert the element to its oxide. After this treatment, the catalyst is ready for use in the dehydrogenation process.

The dehydrogenation process of this invention can be carried out by means of any apparatus whereby there is achieved contact of the catalyst with the mixture of the dehydrogenatable organic compound and oxygen, the process being in no way limited to the use of a particular apparatus. The process of this invention can be carried out using a fixed catalyst bed, fluidized catalyst bed or moving catalyst bed. Presently preferred is a fixed catalyst bed.

Any suitable OXD temperature can be employed which provides the desired degree of catalytic activity in the OXD of the organic feedstock. The OXD temperature will generally be in the range of about 400° to about 705° C. and will more preferably be in the range of about 538° to about 677° C. Generally the higher temperatures are used with lighter reactants and the lower temperatures with the heavier.

The OXD process can be carried out at any suitable pressure. The pressure of the OXD process will generally range from about 0.05 to about 250 psia.

The organic feedstock may be combined with any suitable quantity of free oxygen prior to being passed in contact with the catalyst composition. Preferably, the concentration of oxygen should not exceed the stoichiometric requirement to avoid excessive hydrocarbon oxidation. The concentration of oxygen will generally be in the range of about 0.01 to about 0.5 moles of oxygen per mole of organic feedstock with a concentration in the range of about 0.3 to about 0.45 moles of oxygen per mole of organic feedstock being preferred.

Any suitable feed rate for the organic feedstock can be utilized. The organic feedstock feed rate will generally be in the range of about 200 to about 1200 volumes of gaseous feedstock at standard conditions per volume of catalyst per hour (GHSV) with a feed rate in the range of about 300 to about 600 GHSV being preferred.

The following example is presented in further illustration of the invention.

EXAMPLE

Zinc titanate having the atomic ratio Zn:Ti=1.80 was prepared by combining 80.0 g of Degussa P-25 titanium dioxide and 146.7 g of Mallinckrodt zinc oxide in about 1000 ml of water and mixing for 10 minutes in a blender. The resulting slurry was dried in an oven at 130° C. to remove water and then calcined in air for three hours at 825° C. After cooling, the resulting zinc titanate was crushed and screened and a −16 to +40 mesh fraction obtained for testing and for treatment with various promoters.

Starting with the thus prepared zinc titanate, the catalysts tabulated in Table 1 were prepared by impregnating a weighed portion of zinc titanate with an aqueous solution containing a predetermined weight of the promoting element. The result promoted zinc titanate was dried in an oven at 125° C. and finally calcined in air at 816° C. for 3 hours to convert the promoter to the oxide form. Concentrations cited represent the quantity of promoting element added to the zinc titanate, i.e. 5 wt. % M means the addition of 0.5 g of element M to 10 g of Zinc titanate—not its concentration in the finished catalyst.

TABLE I

| Catalyst | Wt. % Promoter Based on $Zn_2TiO_4$ | Source of Promoter |
|---|---|---|
| 1 | — | — |
| 2 | 1.1 | $Al(NO_3)_3 \cdot 9H_2O$ |
| 3 | 3.0 | $H_3PO_4$ |
| 4 | 1.4 | $Cr(NO_3)_3 \cdot 9H_2O$ |
| 5 | 4.5 | $In(NO_3)_3 \cdot 5H_2O$ |
| 6 | 4.9 | $SnCl_2 \cdot 2H_2O$ |
| 7 | 2.8 | $La(NO_3)_3 6H_2O$ |
| 8 | 6.9 | $Ce(NO_3)_3 \cdot 6H_2O$ |
| 9 | 1.2 | $Sb(C_4H_4O_6)_3 \cdot 6H_2O$ |
| 10 | 8.6 | $Bi(NO_3)_3 \cdot 5H_2O$ |

Catalysts listed in Table I were used to oxidatively dehydrogenate ethane to ethylene. All runs were made at atmospheric pressure and samples were taken when the process was at 700° C.

Runs were made using −16 to +40 mesh portions of catalyst 1–10 to convert ethane to ethylene in a continuous process. A quartz tube reactor containing a coaxially centered thermowell was loaded with 15 mL of catalyst. A 2:1 by volume mixture of air:ethane was passed downflow through the reactor at 1200 GHSV (400 GHSV for ethane only). The quantity of air supplied was about 80% of that required to convert all ethane to ethylene at perfect selectivity. Observed selectivity was always less than 100% because of cracking and production of carbon oxides. The procedure used to make runs was to pass the air-ethane mixture through the reactor while it was being heated. Measurement of the times set forth in Table II started at the time the temperature reached 550° C. Product samples were generally taken and analysed at 50° C. increments. Observed conversion at the lower temperatures was always less than reported in Table II which is data for 700° C. Analyses were made by GLC analyses on snap samples taken from the reactor effluent.

TABLE II

| Catalyst | Promoter | Ethane Converted, % | Selectivity, % | Time, Min. |
|---|---|---|---|---|
| 1 | — | 61.0 | 53.8 | 62 |
| 2 | Al | 65.6 | 60.3 | 68 |
| 3 | P | 41.9 | 76.4 | 42 |
| 4 | Cr | 61.6 | 59.0 | 47 |
| 5 | In | 55.4 | 65.6 | 58 |
| 6 | Sn | 39.8 | 78.0 | 118 |
| 7 | La | 63.0 | 66.7 | 47 |
| 8 | Ce | 59.1 | 69.8 | 47 |
| 9 | Sb | 46.8 | 78.4 | 52 |
| 10 | Bi | 71.2 | 67.5 | 43 |

Unpromoted zinc titanate was effective in converting ethane to ethylene by OXD. The promoters improved the selectivity of the OXD process.

Reasonable variations and modifications are possible within the scope of the disclosure and the appended claims to the invention.

That which is claimed is:

1. A catalyst composition comprising zinc, titanium and a promoter at least one member of which is selected from the group consisting of aluminum, phosphorus, indium, and tin wherein said zinc and titanium are present in said catalyst composition in the form of zinc titanate which is prepared by calcining a mixture of zinc oxide and titanium dioxide in the presence of free oxygen at a temperature in the range of about 650° C. to about 1050° C.

2. A catalyst composition in accordance with claim 1 wherein sufficient oxygen is present in said catalyst composition to satisfy the valence requirements of said zinc, said titanium and said promoter.

3. A catalyst composition in accordance with claim 1 wherein the atomic ratio of zinc to titanium in said catalyst composition is in the range of about 1:1 to about 3:1.

4. A catalyst composition in accordance with claim 1 wherein the atomic ratio of zinc to titanium in said catalyst composition is in the range of about 1.7:1 to about 2.1:2.

5. A catalyst composition in accordance with claim 1 wherein the concentration of said promoter, expressed as an element or mixture of elements, is in the range of about 0.3 to about 10 weight percent based on the weight of said zinc titanate.

6. A catalyst composition in accordance with claim 1 wherein the concentration of said promoter, expressed as an element or mixture of elements, is in the range of about 0.5 to about 5 weight percent based on the weight of said zinc titanate.

* * * * *